United States Patent
Engelberg

Patent Number: 6,063,056
Date of Patent: May 16, 2000

[54] DEVICE AND METHOD FOR ATRAUMATIC DILATATION

[76] Inventor: Moshe Engelberg, 4 Brener Street, Kfar Saba 44349, Israel

[21] Appl. No.: 09/106,128
[22] Filed: Jun. 29, 1998
[51] Int. Cl.⁷ .................................................. A61M 29/00
[52] U.S. Cl. ............................................................ 604/97
[58] Field of Search ............................... 606/192; 604/97, 604/98, 99, 96

[56] References Cited

U.S. PATENT DOCUMENTS

| | | | |
|---|---|---|---|
| 1,235,142 | 7/1917 | Ichilian | 604/97 |
| 3,053,257 | 9/1962 | Birtwell | 604/97 |
| 3,602,226 | 8/1971 | Ericson | 604/98 |
| 4,102,342 | 7/1978 | Akiyama et al. | 604/99 |

*Primary Examiner*—Michael Buiz
*Assistant Examiner*—Kevin Truong

[57] ABSTRACT

A device for intra operative atraumatic dilatation, comprising a rigid tube with an inflatable balloon mounted near one end of the tube and an air bulb mounted near the other end of the tube. The rigid tube together with the balloon and the air bulb form a hermetically sealed volume. In the normal state of the device, the balloon is deflated and the air bulb contains a fluid. In the intestine dilating state, the surgeon applies a pressure on the air bulb, this resulting in a volume of the air in the bulb passing through the rigid tube to the balloon, which is thus inflated. When the surgeon removes the pressure on the air bulb, the device returns to its normal state in which the balloon is deflated. The balloon is made of a generally elastic material which in its deflated state has a diameter similar to that of the tube so that the balloon clasps the tube, to present a low profile so as not to interfere with the insertion of the device into an intestine.

14 Claims, 7 Drawing Sheets

PRIOR ART

PRIOR ART

DEVICE AND METHOD FOR ATRAUMATIC DILATATION

CROSS-REFERENCE TO RELATED APPLICATIONS

There are no related applications filed for the present invention.

STATEMENT AS TO RIGHTS TO INVENTIONS MADE UNDER FEDERALLY SPONSORED R&D

There was no Federal sponsoring for the present invention, therefore there are no rights deriving therefrom.

BACKGROUND OF THE INVENTION

This invention relates to devices for atraumatic intra operative dilatation of an intestine, and more particularly to such devices which include means for dilating each end of the resected intestine segment prior to anastomosis.

At present, a gastro-intestinal operation may include a resection (cutting a segment of intestine apart), with subsequent anastomosis (suturing of the intestine segments).

Suturing may be performed by hand suturing or, in a preferred method, by stapling using a specially devised instrument.

The anastomosis instrument now in use is a circular stapling device, including means for bringing the intestine ends close to each other and in a relative orientation suitable for suturing, and means for applying a plurality of staples to attach the intestine ends to each other, so as to achieve the desired arastomosis.

A problem with the above method is the natural tendency of intestine ends to shrink after being cut apart. That is, after resection both intestine ends tend to contract.

This phenomenon presents a problem to the surgeon: since the intestine has a smaller diameter, a smaller diameter anastomosis instrument has to be used, since a larger diameter instrument may be difficult to insert into the intestine. The instrument is difficult to insert, and it may be difficult to remove after suturing.

Similarly, if manual suturing or other method is used, the suturing will be applied to the small diameter (shrunk) of the intestine end.

It is well known among gastro-intestinal surgeons that a larger diameter anastomosis is preferred, since it results in better performance of the anastomosis in the long run.

However, because of intestine shrinkage, the surgeon has to accept a smaller diameter suture because of the shrunk intestine ends.

A solution to the problem is the use of rigid, metallic cylinders of various diameters, which may be forcibly introduced into the intestine to gradually dilate it.

Various devices available in prior art apparently cannot solve this problem, that is to dilate the intestine to facilitate the performance of a larger diameter anastomosis using an inflating balloon.

Thus, HILDEBRAND J., Patent DD 234228, discloses an implantable external anastomosis splint, which comprises ring of biologically inert spiral steel wire. The implantable external splint is for anastomoses, particularly those of the bile passage. It comprises an external ring of spiral biologically inert steel wire in a number of turns, the internal diameter corresponding to intraoperative requirements. It can also be in the form of a sleeve with peripheral openings.

The patent is not for a removable device, not suitable for the gastro-intestines.

DOMANSKII B. V. et al, Patent SU 1146011, discloses a method of treatment for bile duct cicatricial strictures, comprising repeatedly inflating a balloon. The method of treatment for cicatricial strictures of the bile acts involves forming a bilio-digestive anastomosis on an external drain equipped with an inflatable balloon on the catheter.

The balloon of the catheter is positioned in the lumen of the anastomosis and then once sufficient time has passed for the anastomosis to heal, under x-ray monitoring the balloon is dilated using an x-ray contrastive substance until it takes on the form of an hour glass, and then the balloon is further dilated while maintaining this form as the anastomosis is dilated over the length of the whole period of treatment.

There should be intervals of 5–6 days between the additional dilation cycles of the balloon.

In the above method, an existing anastomosis is dilated in a multi-stage treatment. The present invention, however, relates to a method for achieving a better anastomosis by dilating the intestine prior to anastomosis.

SOLAR R. J., Patent WO 9700094, discloses a method for delivering balloon-expandable stent—involves firmly positioning stent in non expanded form around balloon on distal portion of balloon dilatation catheter. The method involves firmly positioning the stent in non expanded form around the balloon on the distal portion of a balloon dilatation catheter. The distal portion of the catheter is inserted percutaneously into a patient's body to a desired site. The balloon is inflated to cause the stent to expand. The balloon is deflated, and the catheter is removed proximally from the patient's body. The balloon dilatation catheter comprises a catheter shaft defining first and second inflation lumens. Each lumen has proximal and distal ends, and an inflatable dilatation balloon having proximal and distal ends. The distal end of the first lumen opens into and is in fluid communication with the interior of the dilatation balloon. The second lumen extends longitudinally with the first lumen.

The proximal end of the second lumen is adjacent to the proximal end of the first lumen. The second lumen distal end is open and distal to the firs lumen distal end. The section of the second lumen distal to the proximal end of the dilatation balloon is exterior to the dilation balloon. The distal end of the second lumen is open and distal to the distal end of the dilatation balloon. The second lumen sufficiently linear to allow the catheter to be slidingly advanced over a guide wire.

ADVANTAGE—Provides balloon catheter which can apply a focused variable force for dilation, at lower pressures.

Birtwell, U.S. Pat. No. 3,053,257, discloses a catheter or surgical appliance that is adapted to facilitate drainage from a body cavity. It uses a balloon type catheter. The device has an inflatable portion that is adapted to retain and hold the catheter in the position of use when it is inserted into the urethra tube of the patient. The device has a different use than the present invention, and a corresponding different structure to accomplish it.

Thus, the distal end of the body in Birtwell is formed in a generally rounded configuration to allow its entry into the urethra tube.

Additional instruments may be used to hold the intestine dilated during the insertion of a catheter, however such a procedure may require more than one person to perform. There is a coordination problem and the procedure may take more time.

The above and other factors may result in a lower quality operation and may cause post-operation complications.

A very thin device could be inserted into the intestine, however that would not be useful for dilating the intestine that has a much larger diameter. The surgeon may find such a device difficult to use and to locate in the precise position in the intestine, as required.

Moreover, the distal end in Birtwell has an opening or drainage eye therein for drainage purposes, which eye communicates with a longitudinally extending passage in the catheter.

A hollow tube like that in Birtwell may enable contamination due to passage of fecal material through the tube to the operative field. Therefore, it seems that the device in Birtwell may not be suitable for atraumatic dilatation in internal surgery.

The catheter body in Birtwell is made of a flexible material such as plastic. Such a device would keep both hands of a surgeon occupied to operate it. Thus, a surgeon has to insert and hold one end of the device with one hand, while concurrently operating the air pump with the other hand.

During an operation, it is of paramount importance to free a surgeon's hand, that may then be used for other tasks.

The structure in Birtwell does not address the above issues, since it is not intended to be used in internal surgery of the intestine.

Ichilian, U.S. Pat. No. 1,235,142, discloses a syringe adapted especially for the use of women. It has a first bulb filled with air, connected to a second bulb that is normally deflated. When the first bulb is compressed, air will be forced through a neck to the second bulb to inflate it. The purpose of the inflated second bulb is to act as a closure or sealing device for the parts into which said bulb is introduced.

The first and second bulbs are mounted on a discharge tube expanding into a rounded discharge head or nozzle suitably perforated. The tube and head are made of hard rubber or similar material.

The structure in Ichilian is different than that of the present invention and serves a different purpose. Whereas in Ichilian the inflated second bulb acts as a closure or sealing device for the parts into which said bulb is introduced, in the present invention the balloon is to be so shaped as to dilate a shrunken intestine.

In Ichilian, the tube ends in a rounded discharge head or nozzle, that is not suitable for insertion into the shrunk end of an intestine.

In Ichilian, the tube is open to allow the passage of water therethrough and out through its perforated end. An open tube like that in Ichilian may enable contamination due to passage of fecal material through the tube to the operative field.

This structure, therefore, may not be suitable for internal surgery, where it is important to prevent contamination.

Ericson, U.S. Pat. 3,602,226, discloses a self-inflating catheter means to prevent loss of inflation fluid. The purpose of the invention is to improve the shelf life of the device. Another object is to provide a catheter with a removable sleeve or jacket. The jacket may be of a rigid material. It may be made of metal foil or a cohesive film.

The rigid jacket in Ericson is not the part that connects the reservoir and the expanding balloon. Rather, the jacket is only used to contain the inflated reservoir at the proximal end.

In Ericson, the tube that connects the reservoir and the inflatable distal end is apparently flexible. Its function indicates that it should be flexible—the device is inserted into an animal body, with the inflated sleeve within a chamber to be drained such as an animal bladder. To allow its insertion, the tube has to be flexible to adapt to the shape of the animal intestines.

For intestine surgery, it is important to use a rigid tube that will free one of the surgeon's hands, as detailed above. This feature is not provided in Ericson.

The device in Ericson has a main tubular arm with a hollow proximal connecting bell for receiving the drainage tubing connector end and a distal end with a drainage eye or eyes.

This structure may not achieve sterile conditions as required and critical in internal surgery, and may thus endanger the patient. The hollow tube may enable contamination due to passage of fecal material, as detailed above.

The tubular arm in Ericson has to be flexible to allow its insertion into an animal body up to the chamber to be drained. This structure, however, may not allow operation of the device with one of surgeon's hands, as detailed above.

Akiyama et al., U.S. Pat. No. 4,102,342, discloses a valved device used to plug an organic passage such as a person's nasal cavity. As illustrated there, the distal end of the device has no pointed end. Actually it has no solid end at all, rather it has an inflatable balloon.

The pipe in Akiyama that connects the balloon and the air pump is flexible, to adapt to the shape of an internal channel in the body.

As detailed there, the whole device, including the pipe, is made of an elastomer or rubber or an elastic material. Furthermore, a deformable pipe is detailed, that can correspond to the shape of the nasal cavity. Such a structure may not allow operation of the device with one of surgeon's hands.

The balloon in Akiyama cannot be inflated or deflated fast, as decided by the surgeon. Rather, the device in Akiyama has a valve that allows a gradual inflation of the balloon. This structure is devised to keep the balloon in place, while it stops a bleeding for example.

Such a structure is not suitable for the dilatation of an intestine, for several reasons. For example, it may take some time to inflate the balloon, whereas in an operation the surgeon requires a fast acting device to immediately dilate the intestine as required. The valve in Akiyama may prevent the surgeon from feeling the force on the intestine, that is important during a surgery. Moreover, to deflate the balloon the surgeon needs to activate the valve. This may take time and may distract the surgeon's attention during a critical operation. If an intestine is dilated for too long a time, it may be damaged.

MICHEAU P P A, Patent FR 2277566, discloses a catheter for surgical anastomosis, which is dilated after insertion to hold ends for sutures. The sheath of the catheter is slit longitudinally for a short distance, to produce three flexible strips. A steel wire is introduced through the central hole of the catheter, this wire having a ball fixed to its end.

After inserting the tube in the vessel to the point required, the wire is pulled. The ball contacts the end of the sheath and displaces it axially, causing the slit portion to expand and grip the vessel during the suturing process. If required, the free end of the catheter sheath is gripped in a syringe, leaving the wire free.

THIEDE A., Patent DE 4042248, discloses intestine section dilation forceps—has scale indicating valtrac ring size needed simultaneously. The forceps dilate a section of the intestine and simultaneously measure if for a Valtrac ring. Angular jaws dilate the section concerned to maximum to allow insertion of a bio-fragmentary ring, while the necessary ring size is simultaneously read off from a graduated scale. The jaws can be designed so that there is no injury during dilation, while the scale indicates the maximum ring size possible. USE—For intestinal anastomosis.

BOWMAN R. L., Patent WO 9416633, U.S. Pat. No. 5,437,638, details a multifinger topocatheter tip for angioplasty and manipulation—has inflatable tubes attached to lumen at distal end inverted by their respective lumens but can be erected, inflated, deflated etc. by application of fluid.

The catheter (1) has proximal and distal ends and internal lumens which extend between the proximal and distal ends. Adjacent inflatable tubes (6) are attached to The lumens at the distal end of the catheter. There are at least two lumens to which two inflatable tubes are attached and a central lumen for receiving a guide wire or optical fibre.

The lumens comprise between 3 to 13 including a central lumen and inflatable tubes comprises between 2 to 12. ADVANTAGE—Provides a method of dilating narrowed or constricted blood vessels, which recovers target objects, including embroli, from blood vessels.

SUMMERS D. P., U.S. Pat. No. 5,458,573, discloses a toposcopic dilation catheter for insertion into body passageway—has dilatation balloon lumen providing access to balloon carried at distal end of primary catheter shaft.

The toposcopic dilation catheter for insertion into a body passageway, comprises a catheter shaft for inserting into the body passageway, where the catheter shaft includes a distal end, an outer surface and an axial passage extending through it. There is a slide tube coaxially positioned within the axial passage, where the slide tube includes a distal end. There is an everting tube carried within the axial passage, and which has one end bonded to the distal end of the slide tube and the opposite end bonded to the distal end of the catheter shaft, where the everting tube may be everted under fluid pressure.

There is a first balloon carried on the outer surface of the catheter shaft. The balloon may be expanded under fluid pressure. There is a deflection wire extending along the length of the catheter shaft, where the catheter shaft includes a passageway for receiving the deflection wire through it. The deflection wire has a leading end connected to the distal end of the catheter shaft and connected to a thumb actuator at the opposite end of it for manipulating the distal end of the catheter shaft in an angular direction. It also has a second balloon mounted at the distal end of the slide tube, where the one end of the everting tube is bonded to the distal end of the slide tube rearward of the second balloon device. ADVANTAGE—Allows deep penetration of the vascular system even through narrow, totally or partially blocked blood vessels.

SAUNDERS R. J. et al., U.S. Pat. No. 5,525,388, discloses a dilatation balloon—has a constant wall thickness through its working and tapered sections, enabling it to collapse into a very small profile when subjected to a vacuum. A dilatation catheter (10) comprises an elongated shaft (11), a balloon (12) and an adapter (13) at the proximal end of the shaft (11). The shaft has an outer tubular member (14) and a concentric inner tubular member (15) having an inner lumen (16) adapted to receive a guide-wire (17). An annular lumen (18) between the inner (15) and outer (14) tubular members carries inflation fluid to the balloon (12).

The balloon (12) has a cylindrical working section (20) with tapered sections (21,22) at each end thereof terminating in skirt sections (23,24). The working section (20) and tapered sections (21,22) have the same wall thickness, but the skirts (23,24) do not. Skirt (24) is bonded to the distal end of the inner tube (15) whilst the skirt (23) is attached to the outer tubular section (14). The balloon (12) is formed from a parison (30) having a central tubular section (31) leading to parallel ends (34,35). When expanded during blowing the central section (31) forms the working section (20) of the balloon.

USE—Used for a variety of intra-luminal dilatations.

ADVANTAGE—Has constant wall thickness in both the working and tapered sections, enabling it to collapse when a vacuum is applied, into a very small transverse profile along its entire length.

BARRY R. J. et al., Patent WO 9523625, EP 748239, discloses a dilatation procedure for obstructed lumen in the body—uses catheter with cylindrical balloon which has tapering ends of different angles.

The dilatation procedure consists of using a catheter with an inflatable balloon (12) near its distal end. The balloon is generally cylindrical in shape when inflated with sloping proximal (24) and distal (28) ends, the first with a gradual slope and the second with an abrupt slope. During insertion the balloon is wrapped round the catheter (14) in a deflated state and inflated when in position in the obstructed region, and is deflated again and withdrawn after treatment. The balloon is made from a material including an inelastic polymer such as PET.

The angle of taper of its proximal end is about 10 deg., and that of its distal end is about 20 deg. ADVANTAGE—More convenient and atraumatic insertion and removal.

JENDERSEE B. A. et al., Patent WO 9200775, details a transluminal coronary angioplasty catheter with core wire—usable without alteration as fixed, semimovable or movable arrangement.

A catheter comprises a shaft with a main and a secondary lumen, and a balloon extension from the shaft distal end and having inner and outer members, the proximal end of the outer member being continuous with the main lumen and the member distal end forming the catheter distal tip. The outer member has a dilatation balloon formed in a part of its length.

The inner member is connected to the secondary lumen and its distal end terminates in an inflatable seal located within the catheter distal tip. The shaft is pref. of high-density polyethylene and is heat-bonded to the extension which is of linear low-density polyethylene. Pref. a tapered core wire of stainless steel or Ni—Ti alloy and coated with PTFE, silicon or hydrogel passes through the main lumen and outer member and terminates in a radiopaque metal coil.

ADVANTAGE—Can be used as an over-the-wire, fixed-wire or semi-movable wire catheter and changed from one to another at any time, and the seal allows selective fixing of a core wire or purging of air before use.

MATBURN HOLDINGS LTD (MATB-N), Patent DE 1925852, discloses a balloon catheter formed by tube and inflatable bag which are coated with a layer of SBR. GH-. Has two channels. The opening of one of the channels leading outside through the tube wall covered by an inflatable balloon, which is inflated by the entry of a metallised medium through the opening. Thus the tube and the balloon shell have a common external cover layer of SBR.

PUSTOVIT A. A. et al., Patent SU 1220669, discloses a surgical dilator—has perforation at lobe base, and thrust bush in working cavity, formed by lobes.

Perforation is designed in collet (1), at the base of the lobes of the proposed dilator. Thrust bush (3) is positioned in the working cavity, formed by the lobes, and moves along them.

The dilator is introduced into the lumen of a constricted pylorus. Thrust bush (3) is moved to the ends of the lobes by turning feed screw (4). The lobes are parted smoothly due to the screw transmission.

ADVANTAGE—Gives smooth dilation.

BICHOEV K H. et al., Patent RU 2069538, discloses a method for preparing patients for coloplasty following obstructive resection of large intestine—dilating distal end of large intestine daily for 19–23 days.

The procedure consists of carrying out eight dilation cycles of the large intestine daily for 19–23 days in the pre-operative period, each time injecting fluid in a volume equivalent to 110 per cent of that of the stump.

The fluid, an antiseptic solution introduced through the rectum, fills and stretches the stump of the large intestine, making further mobilisation unnecessary during the coloplasty operation, and allowing an end-to-end anastomosis to be formed with the rectum with no technical difficulties. Reduction in post-operative complications.

GRIGORYAN V. A. et al., Patent SU 1835267, technique for producing anastomosis during operations on upper urine canals—using dilatation of distal section of cut ureter by inserting hollow bougie to provide required clearance of distal section.

The proposed technique uses expanding an ureter distal section formed during resection of upper urine conduits. The clearance of ureter distal section is made equal to that of a proximal section by using hollow ureter dilators. As a result larger anastomosis is obtd., while rough structural and functional changes of upper urine canals are avoided.

USE/ADVANTAGE—In urology, for treating stenotic diseases of ureters. Reduced traumatisation and prevention of anastomosis stenosis.

BURLEIGH B. D. et al., Patent WO 9325265, discloses an angioplasty catheter—has dilation balloon on guide wire lumen within infusion lumen having balloon with infusion pores.

Angioplasty catheter (10) can also dispense therapeutic drugs, and comprises a dilation balloon (40) on a guidewire lumen (30) within an infusion lumen (20) carrying a balloon (50) which surrounds the dilation balloon (40) and has infusion pores (58) of size able to infuse insoluble or opt. soluble diagnostic agents, pref. up to 25 microns dia. Specifically pores (58) size range is 15–75 microns, or 15–50 microns, or 35–250 microns, or pres. dia. is 100 microns.

ADVANTAGE—Single catheter has dual function.

Prior art devices and procedures will now be described, to provide a background to the disclosure of the invention.

FIG. 1 details the shape of a resected intestine prior to anastomosis, as in prior art.

A gastro-intestinal operation including a resection may result in a first part of intestine 11, leading to anus, with intestine continuation to anus 14, and a second part of intestine. The subsequent anastomosis (suturing of the intestine segments) includes the suturing of first intestine end 12, to attach to second intestine end. The problem is the shrunk part 13 of first intestine. Bowel near cut area is shrunk because of the resection and a natural tendency of a cut intestine to shrink. The same effect results in the shrunk part of second intestine, near cut area 22.

The same operations are performed in the higher end of the intestine system, that is in the esophagus. There, the first part of intestine 11 leads to the patient's mouth rather than the anus. The operation may be performed in any part of the digestive system.

FIG. 2 illustrates an instrument and method of anastomosis using a circular stapling device as implemented in prior art.

The anastomosis instrument includes a base of instrument for anastomosis 31 using staples and a moving head of instrument for anastomosis 32, so that a gap 33 is formed between base 31 and head 32. A handle or connecting rod to handle 34 is used to handle and operate the device (firing the staples).

The instrument for anastomosis is inserted through intestine 11, so that first intestine end 12 is located just after the end of base 31, inside the gap 33 formed there.

A second part of intestine 21 is brought to the instrument so that it engulfs head 32 and its end 22 is also located in the gap 33.

The procedure as known in prior art involves bringing the ends 12, 22 of the intestines in the state as illustrated, then activating the anastomosis instrument so that head 32 is brought closer to base 31, to close the gap 33 and to bring the intestines ends 12, 22 into physical contact.

In this state, the instrument fires a plurality of staples in locations along the perimeter of head 32, to attach the intestine ends 12, 22 to each other. The anastomosis instrument is then removed, and the sutured intestine is left to recover.

A problem with this prior art procedure is that the intestine is shrunk near the recessed ends 12, 22 as illustrated in intestine regions 13, 23 which have a smaller diameter than the rest of the intestines 11, 21, due to a shrinkage tendency of resected bowels.

In a typical case, whereas the normal (prior to resection) diameter of intestines 11, 21 may be about 2 cm to 3.0 cm (centimeter), the diameter of shrunk intestines 13, 23 may be about 1 cm. This forces the surgeon to use a small diameter anastomosis instrument, since only such a narrow instrument of diameter about 2.5 cm can be inserted into the resected segment. The result is a small diameter anastomosis.

It is known that small diameter anastomosis, performed with a 2.5 cm diameter instrument, often leads to complications and to unsatisfactory recovery after the surgery.

Thus, surgeons would prefer to use a larger diameter instrument, for example a 2.8 cm or 3.1 cm or 3.5 cm diameter instrument. These instruments, however, cannot be inserted into the shrunk intestines, as explained above.

Anastomosis may be performed anywhere in the digestive system.

For example it may be performed in the lower end of the system (near the anus) or the higher end, that is in the esophagus. In the lower end there is room for repairs if there are post-surgery complications, since there is a long intestine which may be cut again and sutured. In the esophagus, however, there is no spare intestine, and there is no room for complications. Complications in an esophagus operation are very difficult to correct.

Therefore, in the esophagus it is still more important to perform a large diameter anastomosis. A 2.5 cm diameter anastomosis is definitely not recommended for operations of the esophagus.

Thus, for anastomosis in any location in the digestive system, the shrinkage tendency of the resected intestine may prevent the performance of a large diameter anastomosis as desired.

SUMMARY OF THE INVENTION

According to the present invention, there is provided a device for atraumatic intra-operative dilatation of an intestine. The device includes means for dilating each end of the resected intestine segment prior to anastomosis.

According to one aspect of the invention, the device for intra operative atraumatic dilatation comprises a rigid tube with an inflatable balloon mounted near one end of the tube and an air bulb mounted near the other end of the tube. The rigid tube together with the balloon and the air bulb form a hermetically sealed volume.

In the normal state of the device, the balloon is deflated and the air bulb is inflated and contains a fluid like air.

In the intestine dilating state, the surgeon applies a pressure on the air bulb, this resulting in a volume of the air in the bulb passing through the rigid tube to the balloon, which is thus inflated. When the surgeon removes the pressure on the air bulb, the device returns to its normal state in which the balloon is deflated.

According to a second aspect of the invention, the balloon is made of a generally elastic material which in its deflated state has a diameter similar to that of the tube so that the balloon clasps the tube, to present a low profile so as not to interfere with the insertion of the device into an intestine.

According to another aspect of the invention, the balloon in its inflated state has a generally cylindrical shape or a generally spherical shape. In another embodiment of the invention, the balloon has a multi-chamber structure.

The end of the tube which is closer to the inflatable balloon has a generally pointed shape, and preferably has a generally conical shape, to facilitate its insertion into the intestine.

The air bulb is secured to the rigid tube to allow the surgeon to handle the whole device with only one hand while holding the air bulb. This enables the surgeon to bring the device with the pointed end (the end close to the inflatable balloon) close to the intestine and to insert that pointed end of the device into the recessed end of the intestine.

The surgeon then can squeeze the air bulb to create a fluid pressure to inflate the balloon, or he/she can release the air bulb to deflate the balloon. The device allows for easy manipulation with one hand and for immediate inflation or deflation of the balloon, as desired by the surgeon.

For use in regular operations, the device has a length of about 10 to 25 cm (centimeters). For use in laprascopy operations, a longer tube is used, having a length of about 25 to 60 cm.

According to still another aspect of the invention, a method for intra-operative atraumatic dilatation is disclosed, comprising the steps of inserting an inflatable balloon mounted on a rigid tube into the shrunk end of a resected intestine, with the balloon deflated; inflating the balloon to dilate the intestine; waiting for several seconds to allow the balloon to achieve the desired effect; deflating the balloon and removing the device from intestine.

Further objects, advantages and other features of the present invention will become obvious to those skilled in the art upon reading the disclosure set forth hereinafter.

DETAILED DESCRIPTION OF THE PREFERRED EMBODIMENTS

Figure 1:
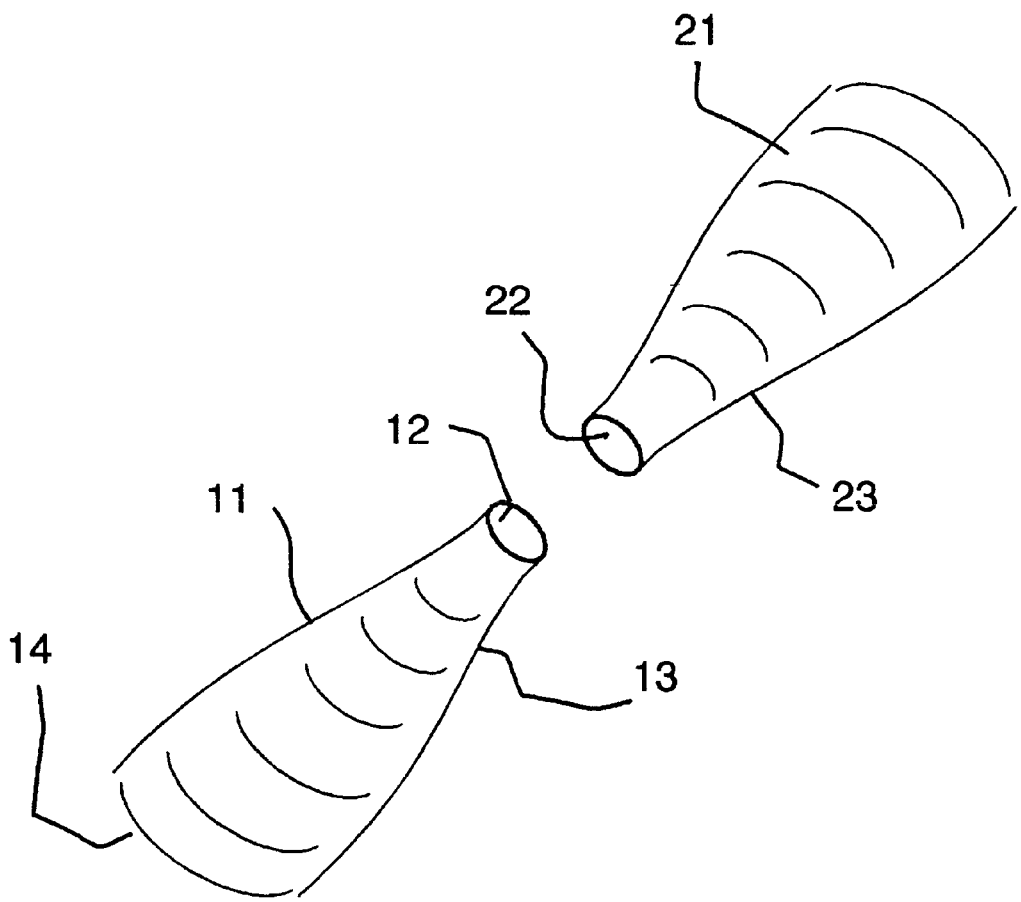
FIG. 1 illustrates the shape of a resected intestine prior to anastomosis, as in prior art.
Figure 2:
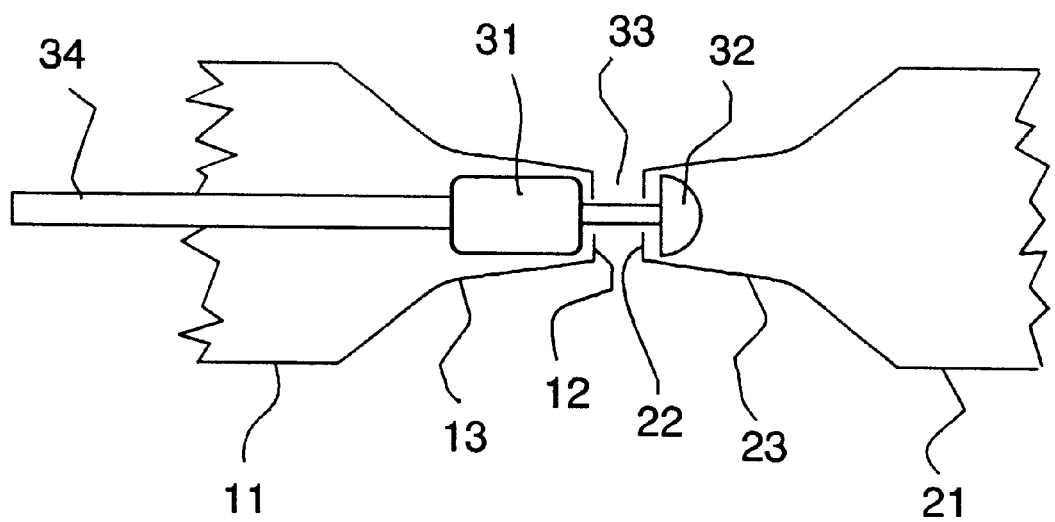
FIG. 2 illustrates an instrument and method of anastomosis using a circular stapling device as used in prior art.

A preferred embodiment of the present invention will now be described by way of example and with reference to the accompanying drawings. FIGS. 1 and 2 relate to prior art and were referred to in the background section.

Figure 3:
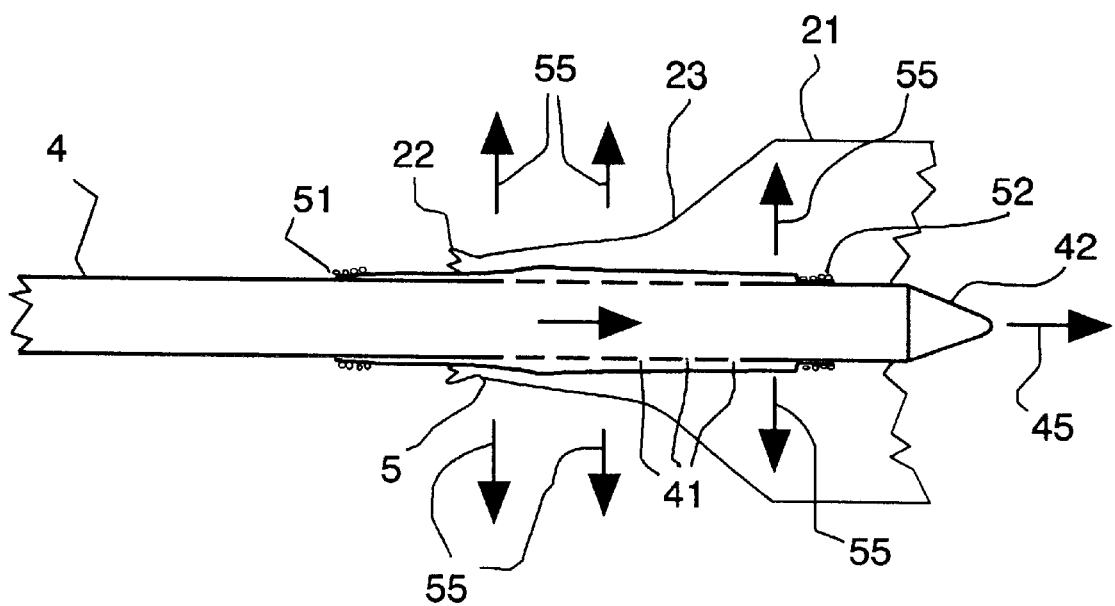
FIG. 3 details a device for intra operative atraumatic dilatation, illustrated in the insertion state.

FIG. 3 details a device for intra operative atraumatic dilatation, illustrated in the insertion state. That is, with the balloon 5 in deflated state. The device is inserted into the second part of intestine 21 through the resected intestine end 22.

The diameter of the device is small, to easily be inserted to the shrunk part 23 of second intestine, near cut area 22 therein.

Balloon 5 is made of a generally tubular surface of an elastic material which is mounted on a rigid tube 4.

The ends of the tube/balloon 51 and 52 are attached to rigid tube 4, to achieve a hermetic seal at the ends of the balloon around the tube 4, so that a sealed volume is achieved between tube 4 and balloon 5.

A sealed volume is required for several reasons.

One reason is that it allows inflating the balloon 5 by applying a force on an air bulb 6(see FIG. 5A). The inflation of balloon 5 is responsive to the force applied on the air bulb 6. This allows a surgeon to immediately inflate or deflate the balloon, as required during a surgery.

Another reason is that it may prevent contamination due to passage of fecal material through a hollow tube to the operative field.

A plurality of holes 41 in tube 4 in the area underneath balloon 5 allow a pressurized fluid in tube 4 to penetrate the cavity between balloon 5 and tube 4, and to inflate the balloon. The fluid may be a liquid or gas.

In a preferred embodiment, one side of tube 4 (the right side in FIG. 3) has a generally conical end 42, capable of easily penetrating the narrow region 23 of intestine 21 without damage to intestine 21.

The other side of tube 4 (leading to the left in FIG. 3) leads to a handle and gas or liquid pressure generating means (not shown, to be illustrated below).

Balloon 5 in its deflated state clasps tube 4, presenting a low profile and thus not interfering with the insertion of the device into intestine 21 through its end 22 and its shrunk part 23.

The balloon 5 may have a generally cylindrical shape, formed around tube 4, with the ends 51 and 52 of balloon 5 being secured to tube 4 so as to form a sealed, hermetically closed cavity under the balloon surface.

Balloon 5 may have various shapes, for example (not shown) a conical or spherical or other form. Balloon 5 may be cylindrical with a pointed end, of a conical shape near the end close to the conical end 42 of tube 4. It is possible to use a multi-chamber balloon, each section when inflated assuming a spherical or cylindrical shape.

Balloon 5 may be made in various dimensions of diameter and length.

Various means may be used to attach the ends of balloon 5 to tube 4. For example, a wire or rope (not shown) wound round the ends of the balloon 5 may be used. The balloon may otherwise be attached with glue, ultrasonic welding, clips devices or other methods.

Since the ends of the balloon 5 are secured to tube 4, the only access means to the inside of balloon 5 are a plurality of holes 41 in tube 4. Preferably, balloon 5 is mounted on tube 4 so as that its right side end 52 is close to the end of tube 42.

In a preferred implementation, the device allows for inserting it to any depth up to about 10 cm inside the intestine 21.

Accordingly, balloon 5 should preferably have a length of about 2 to 6 cm between its ends 51 and 52.

A preferred diameter for tube 4 is about 3 to 12 mm (millimeters). The tube 4 may be made of rigid plastic or polymer material or metal.

Arrow 45 indicates the direction of insertion of the device into intestine 21.

The device for intra operative atraumatic dilatation, including tube 4 and balloon 5 attached thereto, is illustrated after its insertion into intestine 21, and prior to the dilatation procedure. That is, balloon 5 is not inflated as yet.

During a second stage, balloon 5 is inflated so as to expand radially as indicated with arrows 55, to perform the intestine dilatation procedure, as detailed below.

Using the same procedure, the device is also inserted into intestine 11 through its end 12, so that balloon 5 is positioned in the shrunk part 13 of intestine 12. The balloon 5 is then inflated, to dilate the shrunk intestine.

Thus, throughout the present disclosure, any reference to the dilatation of a shrunk end of a intestine is also applicable to the other shrunk end of the intestine.

The device is to be used during any gastro-intestinal operation, as follows: A segment is cut, this resulting in the shrinking of the cut ends. The device is inserted into one shrunk intestine end and the balloon is inflated, until the intestine is dilated.

The dilatation process takes a short time, in the order of several seconds. The balloon is deflated. If the intestine remains dilated, the device is removed and the same dilatation process is performed at the second end of shrunk intestine.

If the surgeon is not satisfied with the resulting intestine diameter, one or more sessions of balloon inflation are performed, until the intestine remains in the dilated state.

After both ends of the intestine are dilated, the anastomosis (suturing of the intestine segments) is performed.

The whole dilatation device should be made of materials suitable for sterilization and for use in the operating room, according to accepted standards. In a preferred embodiment, the device is made of biocompatible materials—US FDA approved.

Figure 4:
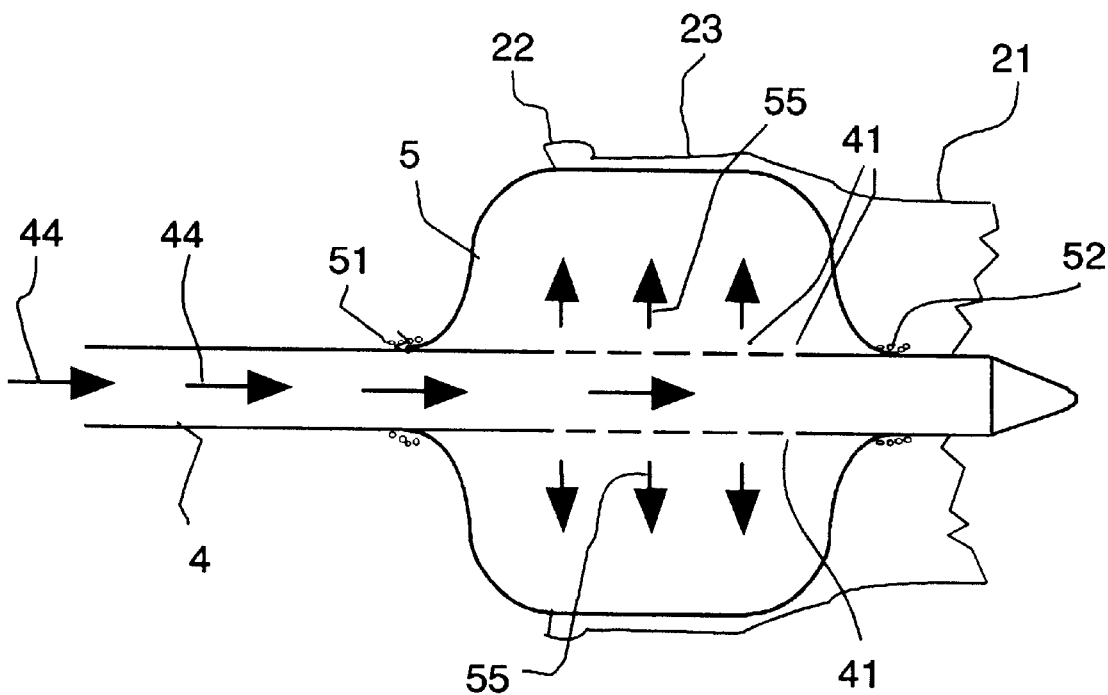
FIG. 4 details a device for intra operative atraumatic dilatation, illustrated in the dilatation state.

FIG. 4 A device for intra operative atraumatic dilatation, illustrated in the dilatation state.

The balloon 5 is illustrated in its inflated state, after insertion through the resected segment. The balloon 5 is still attached to tube 4 at its ends 51, 52. It was inflated through the plurality of holes 41 in tube 4.

Balloon 5 is mounted on rigid tube 4, with its preferably conical end 42 for easier insertion into the intestine resected segment 21 through its end 22 and its shrunk part 23.

The balloon 5 has a generally cylindrical shape, formed around tube 4.

The balloon 5 is inflated through a plurality of holes 41 in tube 4.

A fluid (liquid or gas) under pressure is applied from the left side of tube 4 flowing therein as indicated with arrows 44, to pass through holes 41 and to inflate balloon 5 into the state as shown.

Thus, balloon 5 has been inflated so as to expand radially as indicated with arrows 55, to perform the intestine resected section dilatation. Segment parts 22, 23 are shown in the dilated state, resulting from the force applied by balloon 5.

Advantages: a symmetrical force distribution, to dilate all the parts of the intestine. An uniform radial force is generated. The balloon 5 is soft, does no damage to the resected segment.

By controlling the pressure applied, the dilatation extent can be controlled in real time by the surgeon. Thus, the surgeon applies a fluid pressure until the intestine is dilated to the desired diameter. Then a large diameter anastomosis instrument may be used to perform a circular stapling.

Other anastomosis procedure may be performed, again on a large perimeter of intestine ends 12, 22 and thus resulting in better results.

In a preferred embodiment, the applied fluid is air. Pressurized air is thus applied through tube 4 and holes 41 therein, to inflate balloon 5.

Figure 5:
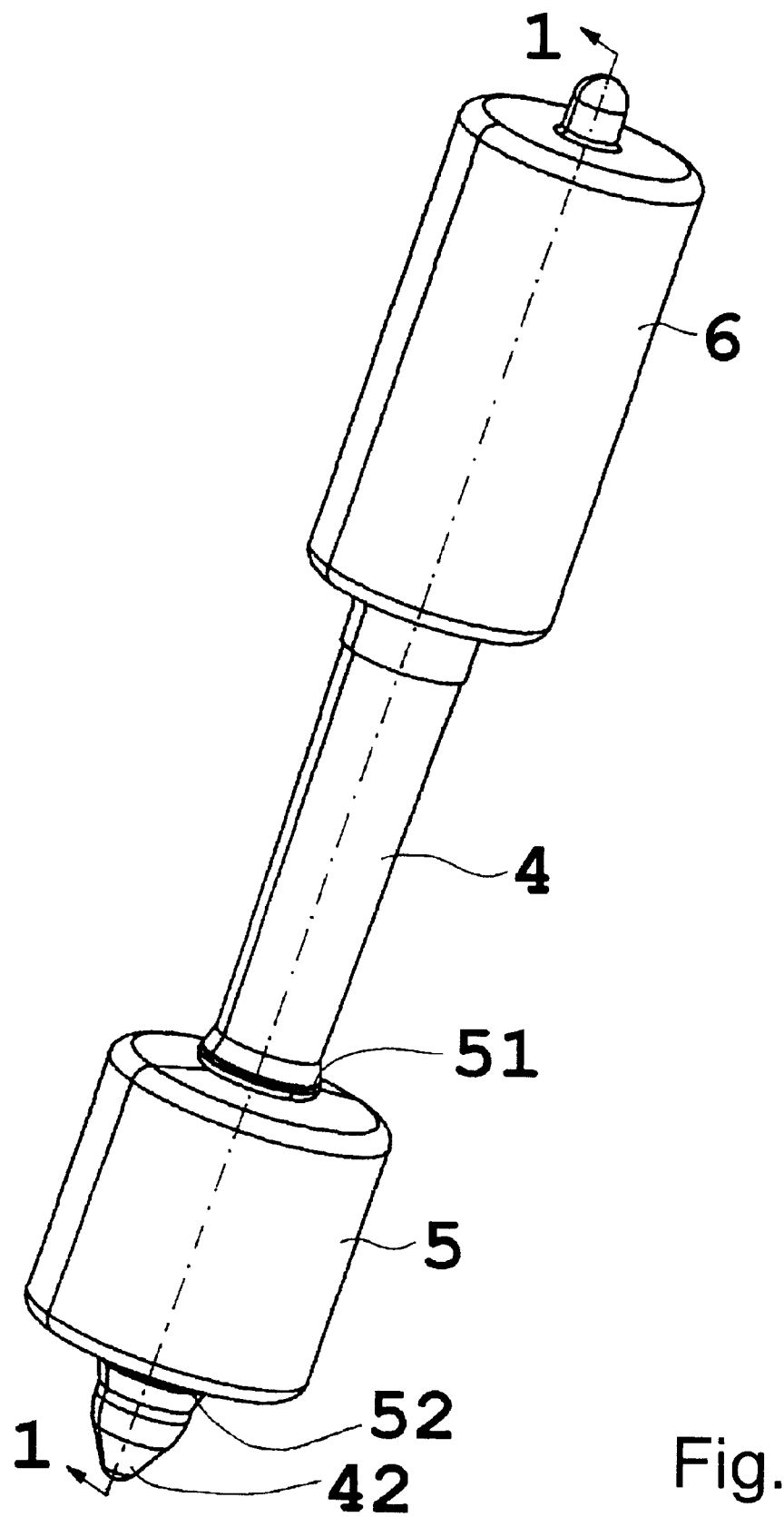
FIG. 5 illustrates an isometric view of a device for intra-operative atraumatic dilatation.

FIG. 5 illustrates an isometric view of the device for intra-operative atraumatic dilatation. For clarity of the description, both balloon 5 and air bulb 6 are shown in their inflated state. In actual use, only one of the above parts will be fully inflated at any given moment. The balloon 5 is attached to tube 4 at the ends 51, 52 of the balloon.

The air bulb 6 is secured to the rigid tube 4 to allow the surgeon (not shown) to handle the whole device with only one hand while holding the air bulb 6. This enables the surgeon to bring the device with the pointed end 42 (the end near the inflatable balloon 5) close to the intestine (not shown) and to insert that pointed end 42 into the recessed end of the intestine.

The surgeon then can squeeze the air bulb 6 to create a fluid pressure to inflate the balloon 5, or he/she can release the air bulb 6 to deflate the balloon 5. The device allows for easy manipulation with one hand and for immediate inflation or deflation of the balloon 5, as desired by the surgeon.

It is very important to allow the operation of the device with just one of the surgeon's hands. This frees his/her other hand for other tasks during the surgery, and may greatly improve the performance of the surgery.

Another advantage is that the surgeon may act fast, with the device responding by inflating or deflating the balloon 5 according to the instantaneous pressure on the bulb 6. This structure may be advantageously used to dilate the intestine by the precise amount of pressure as required, and just for the correct period of time. The required intestine dilatation is thus achieved, while preventing a possible damage to the intestine.

In a preferred embodiment, air bulb 6 contains a volume of about 90 cc of fluid like air, and balloon 5 when inflated contains a volume of about 64 cc of fluid.

For use in regular operations, the device has a total length of about 10 to 25 cm (centimeters). For use in laprascopy operations, a longer tube is used, having a length of about 25 to 60 cm.

Figure 6:
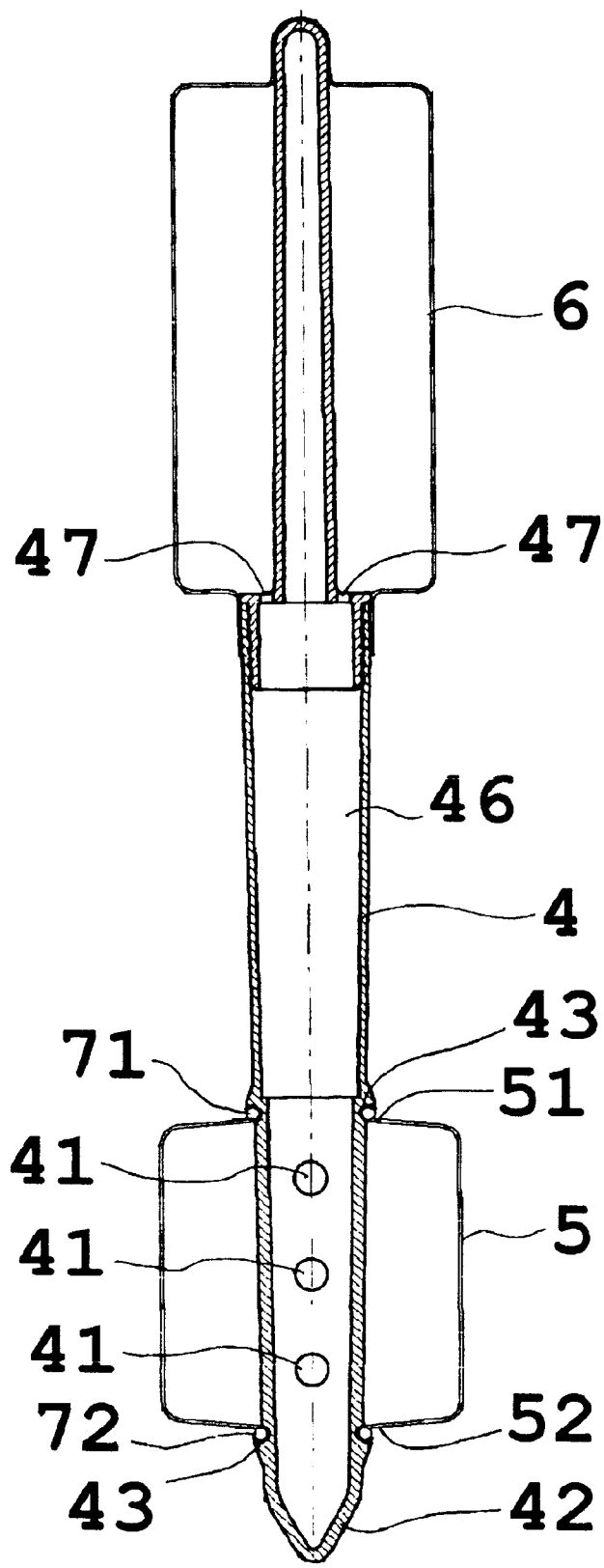
FIG. 6 details a cross sectional view along line 1—1 in FIG. 5 of the device for intra-operative atraumatic dilatation.

FIG. 6 details a cross sectional view along line 1—1 in FIG. 5 of the device for intra-operative atraumatic dilatation.

For clarity of the description, both balloon 5 and air bulb 6 are shown in their inflated state. In actual use, only one of the above parts will be fully inflated at any given moment.

The balloon 5 is attached to tube 4 at the ends 51, 52 of the balloon. In a preferred embodiment, tube 4 has two circular channels or recessions 43 on its outer circumference, to allow a pair of O-rings or rubber rings 71 and 72 each to be placed over one of those channels and one end 51, 52 of balloon 5 to secure each end of balloon 5 to tube 4.

When the user (for example the surgeon) presses bulb 6, then air flows through hole 47, through passage 46 in tube 4 and holes 41 to inflate balloon 5 into the state as shown.

A single hole 41 could be used to inflate balloon 5, however it was found that one hole could get obstructed, this hindering the inflation of balloon 5. Thus, in a preferred embodiment a plurality of holes 41 are used, to ensure the inflation of balloon 5, so as to achieve a more reliable device.

Similarly, one hole 47 could be used, however in a preferred embodiment there are a plurality of holes 47.

Pressurized air is thus applied through tube 4 and holes 41 therein, to inflate balloon 5.

In a preferred embodiment, the applied fluid is air. Thus, air bulb 6 is filled with air, as well as tube 4. Thus, the dilatation device includes one contiguous and hermetically sealed volume, which volume comprises the inside of bulb 6 together with the passage 46 in tube 4 and the cavity 56 between balloon 5 and outer surface of tube 4.

One side of tube 4 preferably has a generally conical end 42, capable of easily penetrating the narrow end of an intestine.

Figure 7A:
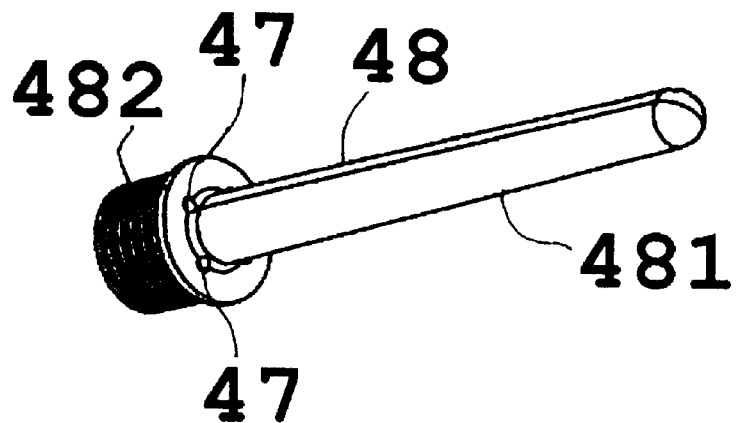
FIG. 7 details the parts comprising the rigid tube, with FIG. 7A detailing the part close to the air bulb and FIG. 7B detailing the part close to the inflating balloon.
Figure 7B:
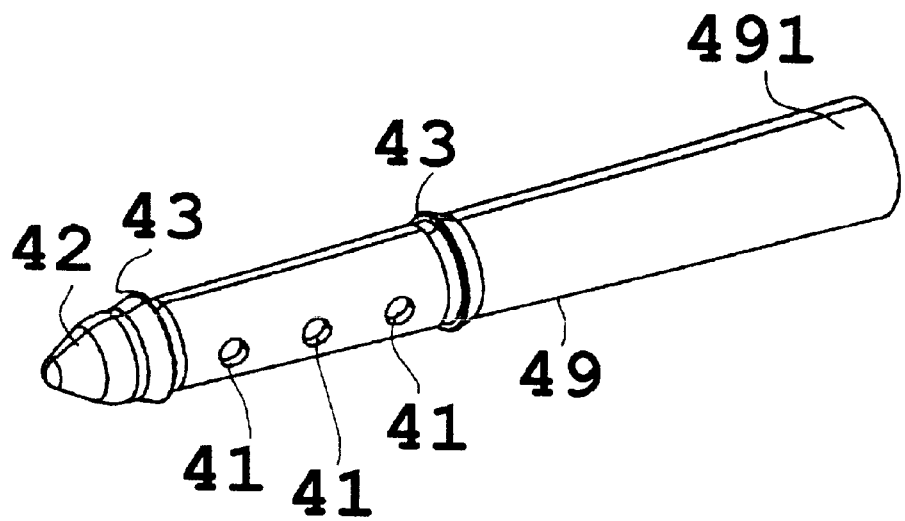

FIGS. 7A and 7B detail the parts 48 and 49 comprising the rigid tube 4 in a preferred embodiment of the invention. FIG. 7A details the part 48 close to the air bulb 6 in FIG. 6.

Part 48 includes an elongate part 481 on which the air bulb is mounted, and a threaded part 482 which couples to the other part 49.

One or more holes 47 are used to transfer the fluid in the air bulb to the balloon, as detailed above.

In a preferred embodiment, the total length of part 48 is about 10 cm and the diameter of part 482 is about 2 cm.

FIG. 7B details the part 49 close to the inflating balloon 5. One end 491 of part 49 has a thread (not shown) corresponding to the thread 482 in part 48, to allow the attachment of parts 48 and 49 to each other to form the rigid tube 4.

One side of part 49 preferably has a generally conical end 42, capable of easily penetrating the narrow end of an intestine.

In a preferred embodiment, part 49 has two circular channels or recessions 43 on its outer circumference, to allow a pair of O-rings or rubber rings (not shown) to be placed over one of those channels to secure each end of balloon 5 to tube 4.

When the user (for example the surgeon) presses bulb 6, then air flows through hole 47, through passage 46 in tube 4 and Holes 41 are used when it is desired to inflate the balloon (not shown), to transfer the fluid used in the device from part 49 to the balloon.

In a preferred embodiment, the total length of part 49 is about 15 cm.

The dilatation device may be disposable, to be thrown away after one use, or may be reusable, with means to allow sterilization.

The dilatation device may be also used in laprascopy operations. For these operations, in a preferred embodiment the tube 4 has a smaller diameter, about 2 to 10 mm. The balloon 5 has a smaller diameter as well. Tube 4 should be longer, about 25 to 60 cm.

Tube 4 may be made of a strong rigid material, like metal or nylon reinforced with glass or carbon fibers for example.

Tube 4 is inserted into the patient body using methods known in the art, for example using a trocar.

Tube 4 has a conical or otherwise pointed end 42, to allow its easy insertion into the shrunk intestine.

It will be recognized that the foregoing is but one example of an apparatus and method within the scope of the present invention and that various modifications will occur to those skilled in the art upon reading the disclosure set forth hereinbefore.

What is claimed is:

1. A device for intra-operative atraumatic dilatation, comprising:
    A. a rigid tube having a first closed end with a generally pointed shape;
    B. an inflatable balloon mounted on the rigid tube near the first end of the tube, and wherein there is at least one hole to form a passage between the inflatable balloon and a passage within the closed rigid tube; and
    C. a bulb mounted near the other end of the tube, wherein there is at least one hole to form a passage between the bulb and the passage within the rigid tube;

and wherein the passage within the rigid tube together with the balloon and the bulb form a hermetically sealed volume, to allow the inflation of the balloon responsive to an instantaneous force applied to the bulb.

2. The device according to claim 1, wherein the balloon is made of a generally elastic material which in its deflated state has a diameter similar to that of the tube so that the balloon clasps the tube, to present a low profile so as not to interfere with the insertion of the device into an intestine.

3. The device according to claim 1, wherein the balloon in its inflated state has a generally cylindrical shape or a generally spherical shape.

4. The device according to claim 1, wherein the balloon has a multi-chamber structure.

5. The device according to claim 1, wherein the closed end of the tube has a generally conical shape with a rounded tip.

6. The device according to claim 1, wherein the balloon has a length of about 2 to 6 cm between its ends on the rigid tube.

7. The device according to claim 1, wherein the balloon in its inflated state has a diameter of about 25 to 60 mm.

8. The device according to claim 1, wherein the tube has a length of about 25 to 60 cm to allow its use in laprascopy operations.

9. The device according to claim 1, wherein the hermetically sealed volume is air filled.

10. The device according to claim 1, wherein the hermetically sealed volume is filled with a liquid.

11. A method for intra-operative atraumatic dilatation, comprising the steps of:
    A. Inserting an inflatable balloon, in its deflated state and that is mounted on a rigid tube, into the shrunk end of a resected intestine, wherein the end of the tube to be inserted first into the intestine has a closed end with a generally pointed shape, and wherein the diameter of the balloon has a diameter similar to that of the tube so that the balloon clasps the tube, to present a low profile;

B. the balloon is inflated by applying a fluid pressure thereto, to dilate the end of the resected intestine, wherein the fluid pressure is generated by applying a force to a bulb mounted on the rigid tube, and wherein the rigid tube with the balloon and bulb mounted thereon allow the use of the device with just one hand;

C. the balloon is kept inflated for a time period as required to allow the intestine to dilate;

D. the balloon is deflated by removing the fluid pressure therefrom, this resulting in the balloon returning to clasp the tube;

E. if the intestine is not dilated enough, repeating steps (C) and (D); and

F. the device including the balloon and tube is removed from the intestine.

12. The method for intra operative atraumatic dilatation according to claim 11, wherein in step (C) the balloon is left inflated for several seconds.

13. A device for laprascopy intra-operative atraumatic dilatation, comprising:

A. a rigid tube having a first closed end, of a length of about 25 to 60 cm;

B. an inflatable balloon mounted on the rigid tube near the first end of the tube, and wherein there is at least one hole to form a passage between the inflatable balloon and a passage within the closed rigid tube; and C. a bulb mounted near the other end of the tube, wherein there is at least one hole to form a passage between the bulb and the passage within the rigid tube;

and wherein the passage within the rigid tube together with the balloon and the bulb form a hermetically sealed volume, to allow the inflation of the balloon responsive to an instantaneous force applied to the bulb.

14. The device according to claim 13, wherein the rigid tube has a diameter of about 2 to 10 mm.

* * * * *